United States Patent [19]

Hüschelrath

[11] Patent Number: 4,924,181
[45] Date of Patent: May 8, 1990

[54] DEVICE HAVING ELECTROMAGNET FOR PROVIDING A MAGNETIC FIELD INCLINED WITH RESPECT TO THE TRANSPORTATION DIRECTION OF A FERROMAGNETIC BODY FOR NON-DESTRUCTIVE, MAGNETIC TESTING OF THE BODY

[75] Inventor: Gerhard Hüschelrath, Laufach-Frohnhofen, Fed. Rep. of Germany

[73] Assignee: Nukem GmbH, Hanau, Fed. Rep. of Germany

[21] Appl. No.: 212,696

[22] Filed: Jun. 28, 1988

[30] Foreign Application Priority Data

Jul. 15, 1987 [DE] Fed. Rep. of Germany ....... 3723360

[51] Int. Cl.[5] ................. G01N 27/82; G01R 33/06; G01R 33/12
[52] U.S. Cl. ................... 324/235; 324/228; 324/242
[58] Field of Search .................. 324/228, 232–243

[56] References Cited

U.S. PATENT DOCUMENTS

| | | | |
|---|---|---|---|
| 2,338,793 | 1/1944 | Zuschlag | 324/243 |
| 4,096,437 | 6/1978 | Kitzinger | 324/235 X |
| 4,477,776 | 10/1984 | Spierer | 324/242 X |
| 4,495,465 | 1/1985 | Tomaiuolo et al. | 324/239 X |
| 4,538,108 | 8/1985 | Huschelrath et al. | 324/235 X |

FOREIGN PATENT DOCUMENTS

| | | | |
|---|---|---|---|
| 3240480 | 5/1983 | Fed. Rep. of Germany. | |
| 200956 | 11/1984 | Japan | 324/228 |
| 639774 | 11/1983 | Switzerland. | |
| 721738 | 3/1980 | U.S.S.R. | 324/240 |
| 827527 | 2/1960 | United Kingdom | 324/236 |

Primary Examiner—Gerald R. Strecker
Attorney, Agent, or Firm—Beveridge, DeGrandi & Weilacher

[57] ABSTRACT

The subject of the invention is a device for non-destructive testing of long bodies (14) for structural faults by means of magnetizing the respective body (14). At least one magnetic field is directed onto the body (14). The structural faults in the body cause changes in the magnetic field pattern. The changes are picked up by magnetic field sensors (50, 52) arranged on or near the body surface. The respective body (14) is moved through the magnetic field, which has an inclination of preferably 45° to the transportation direction (26) of the body (14). The magnetic field sensors (50, 52) are oriented transverse to the direction of the magnetic field.

10 Claims, 2 Drawing Sheets

DEVICE HAVING ELECTROMAGNET FOR PROVIDING A MAGNETIC FIELD INCLINED WITH RESPECT TO THE TRANSPORTATION DIRECTION OF A FERROMAGNETIC BODY FOR NON-DESTRUCTIVE, MAGNETIC TESTING OF THE BODY

BACKGROUND OF THE INVENTION

The invention relates to a device for non-destructive testing of length-adjustable, long ferromagnetic bodies for structural faults by means of magnetizing the respective body, onto which at least one magnetic field is directed and in which structural faults cause in the magnetic field pattern changes that are picked up by magnetic field sensors arranged on or near to the body surface.

Currently available testing systems working on the leakage-flux principle are designed either for longitudinal fault or for transverse fault detection during pipe testing. Rotation testing systems are used mostly for longitudinal fault testing, as they are the obvious choice on account of the required magnetization transverse to the longitudinal axis of the pipe. The magnetic field sensors intersect the stray field lines directly and therefore give an optimum signal if there are faults in the material. Transverse faults cannot be detected with a testing system of this type since these faults run in the field direction and generate practically no leakage flux which might be evaluated. For this reason a transverse fault testing system is required in addition where transverse faults too can occur in test specimens. For this test, a magnetic field is generated in the pipe axis while a stationary set of magnetic field sensors is arranged around the pipe. This means that two complete testing systems with magnetic field sensors and the means for magnetization of the test specimens are necessary for complete testing.

It is also possible to determine the leakage fluxes caused by structural faults without mechanical rotation of the test specimens. To do so, gradient sensors are arranged in at least one row along the circumference of the test specimen, transverse to its direction of transportation. The gradient sensors are connected to an electronic evaluation unit which scans the gradient sensors one after the other. To make the measurement accuracy independent of local static magnetic fields, position-dependent compensation values are assigned to the gradient sensors.

The mechanical rotation of a test sensor of a longitudinal fault testing system is replaced by electronic scanning of the individual sensors. Scanning is inertia-free and therefore does not affect the measuring conditions, as would be the case with a rotating magnetic yoke by induced eddy currents.

SUMMARY OF THE INVENTION

It is an object of the present invention to provide a magnetic device which is capable of detecting structural faults extending in the transportation direction of the body, transverse to the transportation direction, or in between.

The magnetic testing device in accordance with the invention provides a magnetic field through which the respective body is moved having an inclination of more than 0° and less than 90° to the transportation direction of the body and comprises magnetic field sensors oriented transverse to the direction of the magnetic field.

With this device, transverse faults and longitudinal faults are detected as well as faults which are oriented between the transverse and longitudinal faults. The amount of the measured value caused by a fault depends on the projection of the field lines of the leakage flux on the magnetic field sensor surface. Due to the inclination of the direction of the magnetic field in relation to the transportation direction of the respective test specimen, measured values from longitudinal as well as transverse faults will be slightly lower than the measured value obtained when the fault extends in a right-angle to the magnetic field.

The body preferably rotates about its longitudinal axis during movement in the transportation direction. It is possible to detect faults with any orientation direction.

A device according to the present invention comprises an electromagnet having two magnetic pole shoes whose faces are opposite at a distance, by the magnetic pole shoes each having a cutout to permit the body to pass through. The inclination of the faces in relation to the transportation direction of the body is more than 0° and less than 90°. The magnetic field sensors are arranged in the air gap along the outside of the body.

The magnetic testing device according to the invention preferably includes one electromagnet having two magnetic pole shoes that are opposite one another on or near the surface of the body in a zone partially overlapping the body, separated from one another by an air gap, with their faces at an angle of more than 0° and less than 90° to the transportation direction of the body. The zone transverse to the transportation direction of the body has an extent corresponding at least to one turn of the body about its longitudinal axis of 90°. A row of magnetic field sensors in the air gap being arranged corresponding to the extent of the zone transverse to the transportation direction. Means are provided to rotate the body during its displacement in the transportation direction. This device is particularly suitable for bodies of large diameter. It is not necessary with such bodies to provide the magnetic pole shoes closed in the peripheral direction of the body.

The inclination of the faces in relation to the transportation direction should be between 30° to 60° and preferably 45°. In this case, the longitudinal and transverse faults in the body are picked up with approximately 70% of their maximum possible amplitude in each case, i.e. longitudinal and transverse faults are picked up with an attenuation of approx. 3 db. A reduction of such small size is acceptable as a consequence of the possibility of measuring both longitudinal and transverse faults with a device of very simple design. This drawback can, with two orthogonal magnetic gaps, be eliminated by a compensating calculation $\sqrt{X^2 \times Y^2}$ if this is absolutely necessary. The measured values must however be processed dependent on the position.

In a favourable embodiment pole shoe inserts can be fastened in the cutouts or in the pole shoe areas facing the body for adjustment to the external dimensions of the respective body.

A particularly favourable device for implementation of the method proposed in the invention consists of two pairs of magnetic pole shoes arranged in the transportation direction of the body one behind the other, with their faces at a distance from one another, at angles of +45° and −45° in relation to the transportation direction of the body.

With an arrangement of this type it is possible to detect, without rotating the body, those faults that extend in the direction of the magnetic field in the body. In the body position turned 180° these faults are picked up with their maximum possible value. It is favourable for the adjacent magnetic pole shoes of the two electromagnets to at least touch at the ends facing one another. This increases the length of the arrangement.

The magnetic field sensors are preferably Hall-effect gradient sensors to which an electronic evaluation unit is connected.

Further details and advantages of the invention are made clear in the claims and the features to be found therein, singly and/or in combination.

BRIEF DESCRIPTION OF THE DRAWINGS

Further details, advantages and features of the invention are given in the following description of embodiments shown in the drawings.

FIG. 1 shows a vector (10) in a Cartesian coordinate system having an abscissa axis and an ordinate axis, and representing the course of an air gap over a large distance of constant thickness between two magnetic pole shoes. A vector (12) for magnetic induction runs vertical to the vector (10), which is designated B in FIG. 1. A ferromagnetic body (14) shown in FIGS. 2 and 3 and displaced vertically to the drawing plane in FIG. 1 is subjected to this magnetic induction. The body in question is a pipe or bar. The body (14) may have structural faults, for example cracks, shrinkage cavities or holes, henceforward called faults, which have different directions in relation to vectors (10) and (12), for example. In FIG. 1, direction vectors (16), (18), (22) and (24) are given for differently oriented faults. The vectors (16), (24) extend in the ordinate and abscissa directions respectively. The vectors (18), (22) are inclined by 30° and 60° respectively in relation to the abscissa. The faults detected by magnetic field sensors, particularly Hall gradient sensors, are, in the case of vectors (16), (18), (22) and (24) respectively 3 db, 6 db, 6 db and 3 db smaller in relation to the maximum measurable amplitudes resulting from a vertical course of the faults in relation to the magnetic induction B. This results from the projection of vectors (16), (18), (22) and (24) onto vector (10). By this projection, the values for vectors (18) and (22) are about 50% lower than the maximum value, and for vectors (16) and (24) about 70%.

Figure 1:
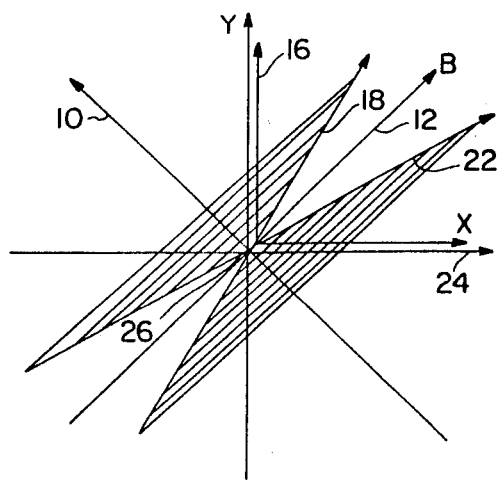
FIG. 1 shows a diagram with vectors for air gap orientation, magnetic induction orientation and various incorrect orientations.

The direction in which the body (14) is moved runs vertical to the drawing plane of FIG. 1 and is numbered (26). This is the longitudinal or transportation direction of the long body (14).

An electromagnet contains a yoke (28) with one winding (30). Two legs (32), (34) that merge into pole shoes (36), (38) are connected to the yoke (28).

The pole shoes (36), (38) each have a cutout (40), (42) through which the body (14) is moved during the test. The cross-sections of the cutouts (40), (42) are adjusted to the dimensions of the body (14), i.e. circular if the body (14) is a pipe or cylindrical bar.

The pole shoes (36), (38) have two faces (44), (46) opposite one another at a constant distance of an air gap (48). The faces (44), (46) are arranged inclined at an angle of 45° in relation to the longitudinal or transportation direction. Magnetic field sensors (50), (52) are arranged on holders, not labelled, in the air gap (48), the sensors preferably being Hall-effect gradient sensors commercially available from Siemens AG, model KSY-20. The planes of the Hall generator faces run in the direction of magnetic induction B.

Figure 2:
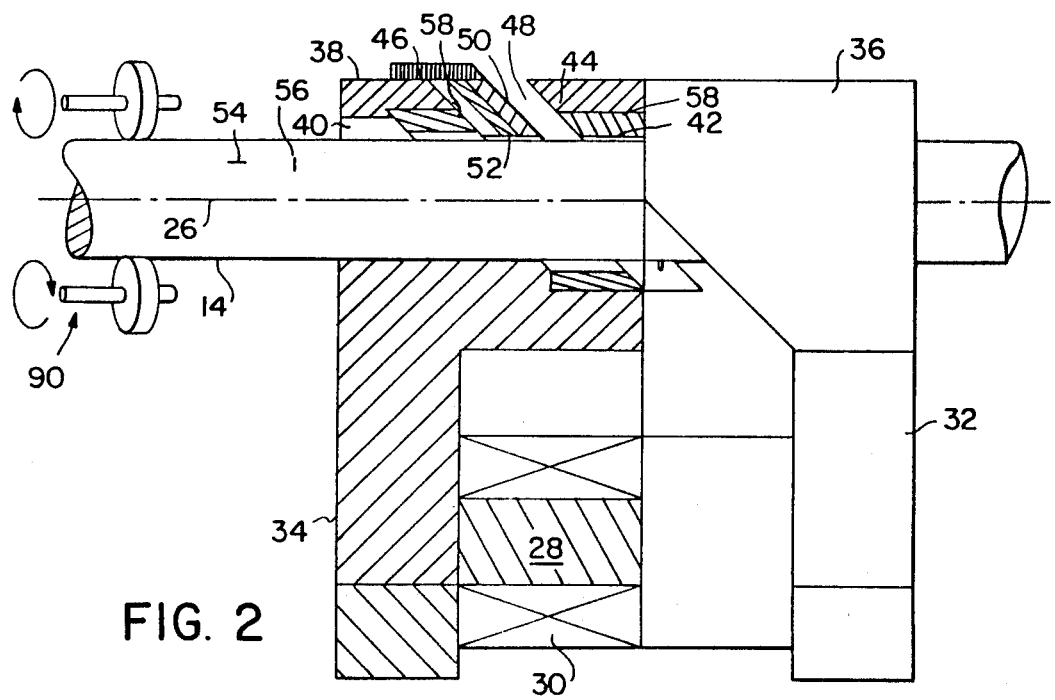
FIG. 2 shows a device for non-destructive testing of ferromagnetic bodies by means of magnetization in side view, partially in longitudinal section.

In the device according to FIG. 2, the relationships between air gap, vector (10) and vector (12) of the magnetic induction are in all other respects as shown in FIG. 1.

Two faults are indicated in FIG. 2 by lines (54) and (56) in the body (14). The fault (54) is a longitudinal fault, i.e. a fault extending in the longitudinal or transportation direction (26) of the body (14). Fault (56) runs transverse to fault (54), i.e. transverse to the longitudinal or transportation direction (26). The two faults (54), (56), represent two extreme positions for faults. Faults (54), (56) are picked up by the magnetic field sensors (50), (52) with the attenuation which was explained in connection with FIG. 1, and further processed by a connected electronic evaluation unit not shown in detail but known per se. The electronic evaluation unit contains, for example, amplifiers connected to the magnetic field sensors and provided behind with multiplexers whose outputs are connected to a microcomputer via a compensation amplifier, to which a compensation value is supplied depending on the position of the magnetic field sensors in the air gap.

An optical display instrument can be connected to the microcomputer.

To accommodate the testing device to bodies (14) with different diameters, pole shoe inserts (58) are provided. The induction generated by the electromagnet is transmitted via the pole shoes (36), (38) to the body (14). The faults (54), (56) and faults whose orientation lies between the orientations of the two faults (54), (56) generate leakage fluxes which are picked up by the magnetic field sensors. To ensure that faults extending in the direction of vector (12) are picked up, the body (14) is rotated in the longitudinal or transportation direction (26) by a rotating means 90. This permits measurement of faults in all directions within the body (14). This method is favourable particularly in pipes with large external diameters, e.g. more than 250 mm. The magnetic field sensors (50), (52) arranged in a row are scanned at a high speed in comparison with the speed of the body (14).

With large diameters the magnetic pole shoes can also be designed so they they do not enclose the entire body (14). Magnetic pole shoes are used here that cover an area on the body (14) which is described by a point on the surface of the body (14) in a 90° rotation about the longitudinal or transportation axis (26). The magnetic field sensors are also arranged in a row along this path. Faults in the body (14) are therefore detectable regardless of their direction. The device also requires a relatively small volume for large diameters.

If rotation of the body (14) is not feasible or too difficult, faults of differing direction can be picked up by twin-gap magnetization. A device for twin-gap magnetization is shown in FIG. 3.

Figure 3:
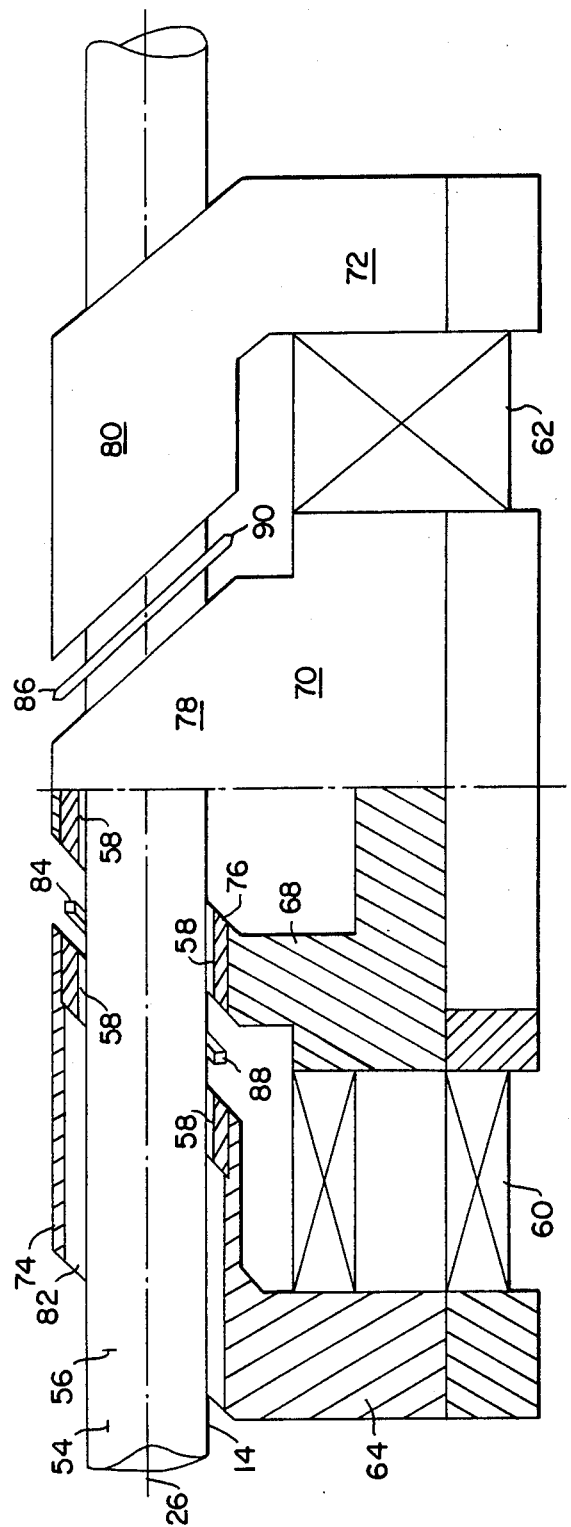
FIG. 3 shows a further device for non-destructive testing of ferromagnetic bodies by means of magnetization in side view, partially in longitudinal section.

The device in accordance with FIG. 3 contains two electromagnets each having one yoke. The yokes are not further identified. There are two coils (60), (62) on the yokes. Legs (64), (68) and (70), (72) respectively are arranged adjacent on both sides of each yoke. The legs (64), (68), (70), (72) merge into magnetic pole shoes (74), (76), (78), (80) respectively, each of the said shoes having a central cutout (82) for passage of the body (14). The faces not identified in detail of the pole shoes (74), (76) and (78), (80) are positioned opposite at constant intervals. Depending upon the diameter of the body 14, pole shoe inserts 58 can be provided as shown in FIG. 3.

The pole shoes (74), (76) and (78), (80) are arranged at inclinations of +45° and −45° respectively in relation to the longitudinal or transportation axis (26). In order to keep the length of the device as small as possible, the pole shoes (76) and (78) of the two legs (68) and (70) merge into one another at those ends facing away from the yokes. Rings of magnetic field sensors (88), (90) are arranged inside the air gaps (84), (86).

The double magnetization ensures, with the two magnetization and scanning planes inclined +45° and −45° in relation to the longitudinal axis, and even without rotation of the body (14), that every fault position is picked up with at least 70% of the maximum indication level.

The device according to FIG. 3 has the additional advantage that there are no restrictions on maximum or minimum testing speed from the measurement standpoint. It is however necessary to have twice the number of sensors and a second yoke. In addition, the installation length increases so that greater pipe tolerances have to be allowed for.

I claim:

1. A device for non-destructively testing a long ferromagnetic body for structural faults by transporting the ferromagnetic body longitudinally through a magnetic field generated by an electromagnet, which field magnetizes the body and extends transverse to the transportation direction of the body so that structural faults in the body cause changes of the course of the magnetic field, which changes are measured by magnetic field sensors arranged on or near to the surface of the body, wherein:

pole shoes of the electromagnet are located on or near to the surface of the body in a zone which covers the body at least partially;

the pole shoes are separated from each other by an air gap;

the pole shoes each have a face which is inclined with respect to an axis defined by the transportation direction of the body;

the faces face each other, are separated from each other by the air gap, and have an inclination angle being greater than 0° and less than 90°;

the pole shoes, in the zone, have at least one portion which extends over a point on a surface of the body to be tested to the location of such point after a rotation of the body around its longitudinal axis by 90°;

a row of magnetic field sensors, corresponding to the extension of the zone, are arranged in the air gap transverse to the transportation direction; and means are provided for rotating the body as the body is transported in the transportation direction.

2. A device for non-destructively testing a long, ferromagnetic body for structural faults by transporting the ferromagnetic body longitudinally through a magnetic field generated by an electromagnet, which field magnetizes the body and extends transverse to the transportation direction of the body so that structural faults in the body cause changes of the course of magnetic field, which changes are measured by magnetic field sensors arranged on or near to the surface of the body, wherein:

the electromagnet is provided with a first pair of pole shoes which pole shoes have faces that are spaced apart to face each other and form an air gap;

the pole shoes of the first pair each have a recess for permitting the body to pass therethrough;

each of the faces of the first pair of pole shoes is inclined with respect to an axis defined by the transportation direction of the body through the recess, the inclination angle being greater than 0° and less than 90°;

the magnetic field sensors are arranged in the air gap and along the outer surface of the body; and in transportation direction of the body, behind the first pair of pole shoes, a second pair of pole shoes are provided, the second pair of pole shoes having recesses for permitting the body to pass therethrough and spaced-apart faces that face each other.

3. A device according to claim 1, wherein the inclination of the faces with respect to the transportation direction is 45°.

4. A device according to claim 2, wherein the inclination of the faces of the first pair of pole shoes with respect to the transportation direction is 45°.

5. A device according to claim 1, wherein a pole shoe insert is provided for being positioned in a recess formed between the pole shoe and the body for accommodating the pole shoe to the external dimensions of the body.

6. A device according to claim 2, wherein pole shoe inserts are provided in the recesses between the pole shoes and the body for accommodating the pole shoes to the external dimensions of the body.

7. A device according to claim 2, wherein the faces of the first pair of magnetic pole shoes are inclined with respect to the transportation direction of the body at an angle of 45°, and the faces of the second pair of pole shoes are inclined with respect to the transportation direction of the body.

8. A device according to claim 2, wherein one of the magnetic pole shoes of the first pair of pole shoes is adjacent one of the pole shoes of the second pair and the adjacent pole shoes touch at their ends that face one another.

9. A device according to claim 1, wherein the magnetic field sensors are Hall-effect gradient sensors.

10. A device according to claim 2, wherein the magnetic field sensors are Hall-effect gradient sensors.

* * * * *